United States Patent [19]

Koban et al.

[11] Patent Number: 4,731,477

[45] Date of Patent: Mar. 15, 1988

[54] PROCESS FOR THE RING CLEAVAGE OF 2-ISOPROPYL-5,5-DIMETHYLTHIAZOLI-DINES SUBSTITUTED IN THE 4-POSITION

[75] Inventors: Hans-Guenter Koban, Gelnhausen; Edgar Koberstein; Juergen Martens, both of Alzenau, all of Fed. Rep. of Germany

[73] Assignee: Degussa Aktiengesellschaft, Frankfurt am Main, Fed. Rep. of Germany

[21] Appl. No.: 18,304

[22] Filed: Feb. 24, 1987

[30] Foreign Application Priority Data

Mar. 5, 1986 [DE] Fed. Rep. of Germany ....... 3607167

[51] Int. Cl.$^4$ ........................................... C07C 149/243
[52] U.S. Cl. .................................................. 562/558
[58] Field of Search ............................... 562/557, 558

[56] References Cited

U.S. PATENT DOCUMENTS

| | | | |
|---|---|---|---|
| 2,477,148 | 7/1949 | Sheehan | 562/558 |
| 3,888,923 | 6/1975 | Asinger | 562/558 |
| 3,946,069 | 3/1976 | Asinger | 562/558 |
| 3,948,984 | 4/1976 | Asinger | 562/558 |
| 4,028,406 | 6/1977 | Asinger | 562/558 |
| 4,045,479 | 8/1977 | Asinger | 562/558 |
| 4,060,548 | 11/1977 | Asinger | 562/558 |

*Primary Examiner*—Michael L. Shippen
*Attorney, Agent, or Firm*—Beveridge, DeGrandi Weilacher

[57] ABSTRACT

A process for the ring cleavage of 2-isopropyl-5,5-dimethylthiazolidines in aqueous acid medium at elevated temperature. Whenever the five ring in the 4-position is substituted by a carboxyl group, penicillamine is the resultant product.

7 Claims, No Drawings

PROCESS FOR THE RING CLEAVAGE OF 2-ISOPROPYL-5,5-DIMETHYLTHIAZOLIDINES SUBSTITUTED IN THE 4-POSITION

The invention relates to a process for the ring cleavage of 2-isopropyl-5,5-dimethylthiazolidine compounds into penicillamine or its derivatives or salts.

Whereas thiazolidine-4-carboxylic acids disubstituted in the 2-position or their alkyl esters, amides or salts can readily be converted into penicillamine or its derivatives or salts by hydrolytic ring cleaving, for example, by brief heating with water, the thiazolidine-4-carboxylic acids monosubstituted in the 2-position or their derivatives or salts are relatively resistant against hydrolytic ring cleavage-Zeit. für Naturforschung. (Journal for Natural Research) 18b, 25, 1963.

It is known to cleave 2-isopropyl-5,5-dimethylthiazolidine-4-carboxylic acid into penicillamine utilizing steam with azeotropic removal of the isobutyraldehyde which forms the equilibrium system. For the quantitative cleavage of the 2-isopropyl-5,5-dimethylthiazolidine-4-carboxylic acid, it is necessary, however, to use large quantities of steam and relatively long reaction times. For the quantitative cleavage of 1 mole of 2-isopropyl-5,5-dimethylthiazolidine-4-carboxylic acid, it is necessary to evaporate for example 20 to 30 liters of water (German patent No. 1 795 297).

It is also known to cleave 2-isopropyl-5,5-dimethylthiazolidine compounds with the help of hydroxylamine (German patent No. 2 142 336).

Still further, it is known that penicillamine may be produced from 2,2,5,5-tetramethyl-thiazolidine4-carbonitrile by converting this nitrile either directly or by way of the intermediate step of the carbonamide into a tetramethyl-thiazolidine-4-carboxylic acid ester, then converting said ester with hydrochloric acid into penicillamine-hydrochloride and then neutralizing the penicillamine-hydrochloride with alkali-Jahrbuch 1967 der Landesamtes für Forschung Nrd. Rh. Westf. (Yearbook 1967 of the Regional Office for Research for North-Rhein-Westphalia) 11 to 35. However, this process is expensive since the carboxylic acid esters must be produced as intermediate products and only small yields are produced. Moreover, the immediate conversion of the tetramethyl-thiazolidine-4-carbonitrile into the salts of the penicillamine did not succeed.

Accordingly, it is an object of the invention to provide a process for ring cleavage of 2-isopropyl5,5-dimethylthiazolidine compounds substituted in the 4-position or their mineral acid salts in aqueous acid medium. In carrying out the process of the present invention, there is employed a compound represented by the standard formula:

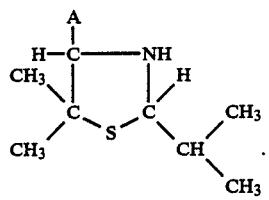

The mineral acid salt of a compound of formula I can also be used in formula I. A represents an N-monoor N-disubstituted carbonamide-or thiocarboxylic acid amide group, which can be substituted by lower alkyl groups of 1 to 6 carbon atoms or by phenyl, or A can be a COOH group. The hydrolysis reaction is carried out at a temperature from 80° to 220° C. under autogenous pressure occurring in an autoclave.

It is possible to carry out the reaction under an inert gas atmosphere. Subsequently, the desired hydrolysis products or their salts are extracted, possibly with an inert organic solvent, from the aqueous phase and isolated in a known manner and optionally the racemate can be separated.

In accordance with the process of the invention, it is not necessary to employ pure starting substances of the general formula I. Mixtures with inorganic salts can be used, for example ammonium salts, such as are obtained as a result of the hydrolysis of the 2-isopropyl-5,5-dimethylthiazolidine-4-nitrile to carboxylic acid.

Included with the mineral acid salts of the 2-isopropyl-5,5-dimethylthiazolidine compounds according to formula I are the hydrohalogenides and especially the hydrochloride.

Preferably, compounds of formula I are employed for purposes of the invention in which A represents the carboxyl group and wherein penicillamine or its salts are obtained as the desired hydrolysis product.

Compounds according to formula I are preferably used in an as high as possible concentration, the specific value of which depends on the specific solubility in the reaction solution.

As an acid medium to be used in the reaction medium in carrying out the inventive process it is preferred to employ aqueous solutions of strong mineral acids such as halogen acids, sulfuric and phosphoric acid. It is advantageous to operate with higher acid concentrations, for example in the case of sulfuric acid with more than 50% by weight, in the case of hydrochloric acid with more than 20% by weight, preferably more than 30% by weight. The ring cleavage with the help of strong acids is carried out at temperatures which range between 80° and 220° C. The chosen reaction temperature at the same time depends on the acid used and its concentration. The reaction times are dependent on the temperature, the acid and its concentration.

In carrying out the process according to the invention, it has been found to be advantageous to proceed in such a way that the 2-isopropyl-5,5-dimethylthiazolidine compound is inserted into the aqueous solution of the strong acid, and which is then heated to the reaction temperature, optionally while stirring and optionally under an inert gas atmosphere. It is recommended to maintain a determined reaction time, since in the case of exceeding an optimal reaction time, the concentration of the desired cleaved product (penicillamine or its derivatives or salts) again decreases. The penicillamine or its derivatives or salts can be obtained from the reaction solution, optionally after shaking with an inert organic solvent, in any conventional manner such as, for example, by evaporating to dryness, and separation of the organic salts through extraction of solvent (German patent No. 1 795 297). The process may be carried out discontinuously as a batch process, as well as continuously, for example with the use of extraction columns.

The DL-penicillamine obtained may be separated into the optical antipodes according to conventional methods, for example, according to the Brucin method. In this case, it is for example advantageous to convert the penicillamine first of all into a compound which is particularly suitable for the racemate separation. For this purpose, the conversion into an acyl derivative of the penicillamine or of the 2,2-disubstituted-5,5-dimethylthiazolidine-4-carboxylic acid is particularly suitable.

The following examples serve to illustrate the invention.

EXAMPLE 1

5.76 g (24 mmole) of 2-isopropyl-5,5-dimethylthiazolidine-4-carboxylic acid . HCl are inserted into 60 ml of 12 n hydrochloric acid and are heated for about 105 min. to 170° C. in an autoclave. After cooling it to room temperature, a content of 19.5 mmole (81.3% of theory) of penicillamine . HCl is found by high pressure liquid chromatographic analysis. The main quantity of the hydrochloric acid is now distilled off until a sump temperature of about 125° C. is reached. After addition of 100 ml of toluene to the sump liquid the rest of the hydrochloric acid or of water is distilled off azeotropically until a sump temperature of about 99° C. has been reached. After cooling off, 40 ml of acetone are added and the mixture is brought to a temperature of 70°-80° C. After a short time, 2,2,5,5-tetramethyl-thiazolidine-4-carboxylic acid . HCl is precipitated and is filtered off and dried after 3 hours. There is obtained 4.0 g (73.8% of theory) of pure 2,2,5,5-tetramethyl-thiazolidine-4-carboxylic acid . HCl with a melting point of 206°-208° C.

EXAMPLE 2

The procedure as described in Example 1 is followed, however there is used 11.52 g (48 mmole) of 2-isopropyl-5,5-dimethylthiazolidine-4-carboxylic acid HCl in 60 ml of 12 n hydrochloric acid and the reaction time extends to about 120 min. By high pressure liquid chromatographic analysis, there is determined to be 37.5 mmole (78.1% of theory) of penicillamine HCl. By following analogous processing, as in Example 1, there is obtained 7.96 g (73.4% of theory) of pure 2,2,5,5-tetramethyl-thiazolidine-4-carboxylic acid . HCl with a melting point of 206°-208° C.

EXAMPLE 3

11.52 g (48 mmole) of 2-isopropyl-5,5-dimethyl-thiazolidine-4-carboxylic acid . HCl are inserted into 60 ml of 12 n hydrochloric acid and are heated in an autoclave for about 120 min. to 170° C. After cooling to room temperature, there is found by high pressure liquid chromatographic analysis a content of 39 mmole (81.3% of theory) of penicillamine . HCl. The solution is shaken once with 10 ml of chloroform and the aqueous phase is concentrated to dryness using a rotation evaporator. The residue is dissolved in 70 ml of 96% ethanol and the pH of the solution is adjusted with the help of triethylamine in ethanol to a pH value between 6 and 7. After a short time, the penicillamine separates. After drying, there is obtained 5.46 g (76.3% of theory) of penicillamine with a melting point of 201°-204° C.

EXAMPLE 4

A 0.8 molar solution (0.8 mole/1) of 2-isopropyl-5,5-dimethylthiazolidine-4-carboxylic acid . HCl is heated in 12 n of hydrochloric acid in an autoclave. The reaction time and the reaction temperature are varied. After cooling, the yield of penicillamine . HCl is determined by high pressure liquid chromatographic analysis. The results are summarizsed in Table 1:

TABLE 1

| Reaction Temperature (°C.) | Reaction Time (min.) | Yield (%) |
|---|---|---|
| 150 | 160 | 38.1 |
|  | 250 | 59.4 |
|  | 340 | 69.4 |
|  | 490 | 63.8 |
| 170 | 105 | 78.1 |
|  | 135 | 83.1 |
|  | 165 | 69.4 |
|  | 195 | 46.9 |
| 190 | 60 | 68.8 |
|  | 75 | 64.6 |
|  | 90 | 43.8 |

EXMAPLE 5

A 0.8 molar (0.8 mole/1) solution of 2-isoprophyl-5,5-dimethylthiazolidine-4-carboxylic acid . HCl is heated in 47% hydrobromic acid to 170° C. in an autoclave. The reaction time is varied. After cooling, one determines the yield of penicillamine. HCl by high pressure liquid chromatographic analysis. The results are summarized in Table 2:

TABLE 2

| Reaction Time (min.) | Yield (%) |
|---|---|
| 75 | 75 |
| 100 | 77.1 |
| 120 | 70.8 |
| 140 | 71.9 |

EXAMPLE 6

A 0.8 molar (0.8 mole/1) solution of 2-isopropyl-5,5-dimethylthiazolidine-4-carboxylic acid. HCl is heated in an autoclave in 75% sulfuric acid. The reaction time and the reaction temperature will be varied. After cooling, the yield of penicillamine . HCl is determined by high pressure liquid chromatographic analysis. The results are summarized in Table 3:

TABLE 3

| Reaction Temperature (°C.) | Reaction Time (min.) | Yield (%) |
|---|---|---|
| 130 | 75 | 25.0 |
|  | 135 | 43.8 |
|  | 195 | 45.0 |
| 140 | 45 | 33.3 |
|  | 75 | 55.8 |
|  | 105 | 50.0 |
| 160 | 30 | 35.0 |
|  | 45 | 33.3 |
|  | 60 | 25.0 |

By following the procedures set forth in Examples 1-6 it is possible to obtain corresponding products when using compounds wherein A is an N-mono, or N-disubstituted carbonamide or thiocarboxylic acid amide group.

Further variations and modifications of the present invention will be apparent to those skilled in the art from the foregoing and are intended to be encompassed by the claims appended hereto.

The German patent application No. 36 07 167.6 is relied on and incorporated herein by reference.

We claim:

1. A process for the ring cleavage of a 2-isopropyl-5,5-dimethylthiazolidine compound substituted in the 4-position or mineral acid salts thereof comprising hydrolyzing in an aqueous acid medium, a compound represented by structural formula:

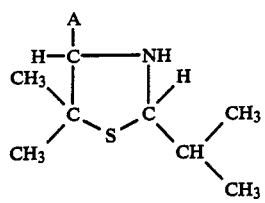
(I)

or a mineral acid salt therof,
wherein A represents COOH, or an N-mono- or N-disubstituted carbonamide or thiocarboxylic acid amide group wherein the substituent is lower alkyl with 1 to 6 carbon atoms or phenyl,
at a temperature from 80° to 220° C. under autogenous pressure in an autoclave.

2. The process according to claim 1, wherein A is COOH and penicillamine is recovered as the product.

3. The process according to claim 1, wherein an aqueous sulfuric acid solution with a concentration of >50% by weight of sulfuric acid is used as the acid medium.

4. The process according to claim 1, wherein a hydrochloric acid solution with >20% by weight of hydrochloric acid is used as the acid medium.

5. The process according to claim 2, wherein an aqueous sulfuric acid solution with a concentration of >50% by weight of sulfuric acid is used as the acid medium.

6. The process according to claim 2, wherein a hydrochloric acid solution with >20% by weight of hydrochloric acid is used as the acid medium.

7. The process according to claim 1, wherein the said compound is introduced into a solution of a mineral acid.

* * * * *